(12) United States Patent
Wheeler

(10) Patent No.: US 6,197,309 B1
(45) Date of Patent: Mar. 6, 2001

(54) PROSTATE FORMULA

(76) Inventor: Ronald E. Wheeler, 412 C.R. 243, Durango, CO (US) 81301

(*) Notice: Subject to any disclaimer, the term of this patent is extended or adjusted under 35 U.S.C. 154(b) by 0 days.

(21) Appl. No.: 09/368,297

(22) Filed: Aug. 3, 1999

Related U.S. Application Data

(60) Provisional application No. 60/095,202, filed on Aug. 3, 1998.

(51) Int. Cl.$^7$ .......................... A61K 35/78; A61K 33/32
(52) U.S. Cl. ....................................... 424/195.1; 424/641
(58) Field of Search .................................. 424/195.1, 641

(56) References Cited

U.S. PATENT DOCUMENTS

| | | |
|---|---|---|
| 3,856,946 | 12/1974 | Debat . |
| 4,258,037 | 3/1981 | Juvin . |
| 4,263,316 | 4/1981 | Thominet et al. . |
| 4,364,867 | 12/1982 | Thominet et al. . |
| 4,549,990 | 10/1985 | Seguin et al. . |
| 5,264,428 | 11/1993 | Streber . |
| 5,543,146 | 8/1996 | Perez . |
| 5,547,673 | 8/1996 | Bombardelli . |
| 5,565,214 | 10/1996 | Zambo et al. . |
| 5,580,857 | 12/1996 | Oden . |
| 5,665,393 | 9/1997 | Chen et al. . |
| 5,736,144 | 4/1998 | Gideon . |
| 5,976,568 * | 3/2000 | Riley ..................................... 424/451 |
| 6,039,950 * | 3/2000 | Khwaha et al. ................... 424/195.1 |

FOREIGN PATENT DOCUMENTS

9701051 * 5/1999 (HU) .

OTHER PUBLICATIONS

Brown, Donald J., "Benign Prostate Enlargement" *Herbal Prescriptions for Better Health; Your Everyday Guide to Prevention, Treatment and Care* (1996).

Brown, Donald "Saw Palmetto Extract in the Treatment of BPH" *The Journal of the American Botanical Council and the Herb Research Foundation* No. 34 (Summer 1995).

Wilt, Timothy J. et al, "Saw Palmetto Extracts for Treatment of Benign Prostatic Hyperplasia" *Journal of the American Medical Assoc.* 280:18:1604–1609 (1998).

Zand, Janet et al, "Optimal Prostate Health With Natural Medicine" Health World Online (1996).

"Newly Approved Drug Therapies" CenterWatch, Inc. (1997).

"Liquid Products" Hankintatukku Natural Health Products Co. (1998).

Combs, G. F., Jr., et al. "Reduction of Cancer Mortality and Incidence by Selenium Supplementation" *Medizinische Klink*, 92 Suppl. 3, pp. 42–45 (1997).

Pinto, John T., et al. "Garlic and Prevention of Prostate Cancer. Nutriceuticals: Des. Foods III, 3$^{rd}$, pp. 177–187" (1997), cited in *Chemical Abstracts*, vol. 127, No. 25 (Dec. 22, 1997), abstract No. 345615, p. 504.

Key et al. Br. J. Cancer, vol. 75, No. 5, pp. 678–687, May 1997.*

Pinto et al. Nutraceuticals [Course Des. Foods Proc.], 3rd, pp. 177–187 (abstract enclosed), 1997.*

Sigounas et al. Nutrition and Cancer, vol. 27, No. 2, pp. 186–191 (abstract enclosed), Feb. 1997.*

Troll et al. Amticarcinogenesis and Radiation Protection, 4th Intl. Conf. (abstract enclosed), Apr. 1993.*

\* cited by examiner

*Primary Examiner*—Christopher Tate
(74) *Attorney, Agent, or Firm*—DeWitt Ross & Stevens SC

(57) ABSTRACT

A composition providing an all-natural, non-surgical preventative of or improvement to disorders of the prostate gland is described. The invention relates to a composition for the prevention of or improvement of prostatitis, and for relieving symptoms and improving objective signs of prostatitis. The formula of the composition preferably includes the following ingredients each in a therapeutically effective amount: Vitamin C, Vitamin B6, Vitamin E, zinc, glycine, L-alanine, Glutamic acid, Saw palmetto, Pygeum extract, Pumpkin seed, Stinging nettle, Echinacea, garlic, Ginkgo leaves, and selenium.

16 Claims, 5 Drawing Sheets

PROSTATE FORMULA

Priority is hereby claimed to provisional application Ser. No. 60/095,202, filed Aug. 3, 1998, and incorporated herein by reference.

FIELD OF THE INVENTION

The present invention relates generally to a composition that provides an all-natural, non-surgical preventative of or improvement to disorders of the prostate gland. More specifically, the invention relates to a composition for the prevention of or improvement of prostatitis, and for relieving symptoms and improving objective signs of prostatitis.

DESCRIPTION OF THE RELATED ART

The prostate gland (or prostate) is a walnut-sized, mucous-producing organ in males that lies just below the urinary bladder. The prostate typically grows and enlarges throughout life. The only known function of the prostate is to produce a secretion that nourishes and protects the sperm during reproduction. The urethra, the canal that in most mammals discharges urine from the bladder, passes through the prostate gland. Unfortunately, this anatomical feature creates problems, often associated with difficulty in urination, as males age.

In men, the prostate gland is the source of several common disorders including prostatitis and benign prostatic hypertrophy (BPH), wherein the prostrate gland becomes inflamed or enlarged. Prostatitis is defined as an inflammation or infection of the prostate gland. While prostatitis may be acute, associated with systemic findings of fever, chills and rigors, most cases of prostatitis are chronic and tend to be incurable with relatively frequent recurrences despite optimal standard therapy. Chronic prostatitis (inflammation or infection of the prostate) is common to all adult men. It is associated with virtually all cases of prostate cancer and is present in every prostate biopsy regardless of other findings. Chronic prostatitis may not cause significant symptoms in many men, but in others it can be a devastating disease that severely affects the quality of life of those afflicted. It is difficult to diagnose and even more difficult to treat.

The most common symptom of chronic prostatitis is pelvic pain, followed by various voiding symptoms, impotence, and infertility. Pain from prostatitis is usually located in the groin, testicles, and penis, just above the rectum or in the suprapubic area over the bladder. Pain is frequently associated with ejaculation. Typical voiding symptoms produced by prostatitis include getting up at night to void (nocturia), frequency and urgency of urination, incomplete voiding, decreased force of the urinary stream, intermittency of the stream and a need to push or strain to void. Impotence or erection difficulties and male infertility are also associated with prostatitis.

A wide variety of therapies are available, but few actually work in more than a small percentage of cases. None of the standard treatments is able to improve the health and well being of the prostate.

In the treatment of prostatitis, physicians have traditionally recommended everything from doing nothing to multiple and extended courses of antibiotics, other drugs, and lifestyle changes. Those patients who truly have an identifiable infection of the prostate benefit from antibiotics. These need to be continued for at least 6–12 weeks and, in some cases, long-term or indefinite antibiotic suppression therapy is necessary.

BPH occurs naturally in most males over 50 years of age. At this age, the male body begins to transform testosterone (male sex hormone) into dihydroxytestosterone (DHT) at higher levels within the prostate. This is primarily due to the higher levels of the enzyme reductase, which causes the conversion of testosterone to DHT. DHT has a tendency to bind to prostatic receptor cells, which ultimately results in prostate enlargement. It is usually a benign condition, and therefore, in some cases there is no need for surgery. However, enlargement of the prostate gland can cause many uncomfortable and annoying symptoms. Worsening symptoms may require prostate surgery. Nearly 400,000 prostate surgical procedures are performed annually to treat enlarged prostates. Numerous laboratories are conducting research in an attempt to find a cure for BPH.

Treatments for prostate disorders include alpha blockers, e.g., HYTRIN (terazosin HCl, Abbott Laboratories, Abbott Park, Illinois), CARDURA (Roerig Pharmaceuticals, Alexandria, Virginia) and FLOMAX (tamsulosin HCl, Boehringer Ingelheim Pharmaceuticals, Ridgefield, Conn.), which are designed to relax the muscle tension in the prostate and improve urinary flow. They do tend to improve voiding difficulties and relax tension in the prostate. However, they are expensive, need to be taken indefinitely in high doses, may often have significant side effects and do not cure the underlying problem or prevent recurrences.

There are also other treatments for prostate disorder. For example, PROSCAR (finasteride, Merck Human Health, White House Station, N.J.) can shrink prostate tissue, but there is no proof it helps in the treatment of prostatitis. Allopurinol, a drug that reduces uric acid levels in the body, has been used to treat prostatitis based on the theory that uric acid crystals may form in the prostate and cause inflammation. Anti-inflammatory agents, such as ibuprofen, and hot sitz baths have been helpful in treating the discomfort caused by prostatitis in many patients, but neither of these treatments actually cures the disease and the benefits wear off rapidly.

Irritative voiding symptoms may be relieved by bladder relaxing agents such as oxybutynin (DITROPAN Alza Corporation, Palo Alto, Calif.), while antidepressants such as amitriptyline (ELAVIL AstraZeneca, Wilmington, Del.) have been helpful in various chronic pain conditions such as prostatitis associated with depression. Biofeedback, behavioral therapy, referral to a pain clinic and psychological treatment have all been recommended for patients with prostatitis and occasionally offer some relief to selected individuals. For the most part, current treatment methods for prostatitis are generally rather disappointing.

Prostatic massage plus antibiotics has been used with some success. However, proponents of prostatic massage (championed in the Philippines) have little reproducible data to support their methods. Other drawbacks include intense discomfort/pain at the time of massage, the need for accurate cultures of the prostatic fluid, and a dependence on antibiotics to ultimately effect the cure.

There are natural elements that have known benefits in treating enlargement of the prostate gland and prostatitis. It is widely accepted that zinc has positive effects in reducing an enlarged prostate, but studies have indicated that zinc administered orally does not reach prostatic tissue very effectively. Therefore, the prostate does not reap its full benefits. Other studies have shown that *Pygeum africanum* extract has definite effects in reducing the size of the prostate.

Extensive studies have shown that Saw palmetto (*Serenoa repens*) effectively reduces the size of the enlarged prostate and restores function. T. J. Wilt et al. recently reviewed 18 randomized controlled trials involving the effects of saw palmetto on 2,939 men and found that the evidence suggests that *S. repens* (Saw palmetto extract) improves urologic symptoms and flow measures, and that when compared with PROSCAR, *S. repens* produces similar improvement in urinary tract symptoms and urinary flow and was associated with fewer adverse treatment events. T. J. Wilt et al., "Saw Palmetto Extracts for Treatment of Benign Prostatic Hyperplasia," *JAMA* 280:1604–09 (1998). The Saw palmetto berry contains oil composed of sterols and various saturated and unsaturated fatty acids from which the purified, fat soluble extract are used medicinally.

Another natural product known to produce beneficial effects on the enlarged prostate is pumpkin seed. Pumpkin seeds have been used as a folk remedy for centuries, and it is believed that Hungarian gypsies, Ukrainians and Transylvanians do not suffer from BPH because they eat pumpkin seeds from childhood as part of their daily diet. Additionally, the Chinese use a combination of three amino acids: glycine, L-alanine, and glutamic acid, to treat disorders of the prostate.

PROSTAMAX (Hankintatukku Natural Products Co., Helsinki, Finland) is a prostate formula on the market, having a per tablet formula of Vitamin C, 10 mg; Vitamin B6, 10 mg; Vitamin E (succinate), 5 IU; zinc chelate, 10 mg; L-glycine, 120 mg; alanine, 120 mg; Saw palmetto, 106 mg; *Pygeum africanus* extract, 10 mg; *Pygeum africanus* herb, 20 mg; pumpkin seed, 200 mg; Stinging nettle leaves, 75 mg; Echinacea, 25 mg; Ginkgo biloba, 20 mg; Wild yam, 20 mg; and Uva ursi, 10 mg.

U.S. Pat. No. 5,736,144 to Gideon describes a medicinal tea made from radishes. The tea is used as an anti-microbial or anti-inflammatory agent and is reportedly effective in treating prostatitis.

U.S. Pat. No. 4,258,037 to Juvin describes a therapeutic composition useful for the treatment of both male and female urogenital disorders such as prostatic disorders and bartholinitis. The composition contains Pygeum or other extracts of the trees of the Rosaceae family, together with a mono-aminated amino acid such as glycine, L-glutamic acid or L-alanine.

U.S. Pat. No. 5,543,146 to Perez describes a dietary supplement composition for alleviating the symptoms associated with enlargement of the prostate gland. The composition includes pumpkin seeds, zinc, magnesium, vitamin E, Saw palmetto, and *Pygeum africanum*, but does not include stinging nettle, zinc, garlic ginkgo, glutamic acid, alanine, glycine, Echinacea and Uva ursi.

There is thus a need for a composition that shows improved effectiveness in the use for prostate disorders. Further, there is needed a method of improving or preventing prostate disorders, and of maintaining prostate health.

SUMMARY OF THE INVENTION

The primary object of the invention is to provide a formula having beneficial effects in preventing and improving prostate disorders.

It is also an object of the invention to provide a formula that is beneficial to bladder health in women documented by a reduction in urgency and frequency, indicative of improved bladder stabilization.

It is a further object of the invention to provide a prostate formula that has all natural ingredients, has no adverse side effects, and has no interactions with any medication.

It is a further object of the invention to provide a method of preventing and improving prostate disorders and of maintaining prostate health These objects are satisfied by providing a formula comprising a therapeutically effective amount of at least one antioxidant, a therapeutically effective amount of at least one anti-inflammatory, a therapeutically effective amount of at least one immunity booster, a therapeutically effective amount of pytosterol, a therapeutically effective amount of garlic, a therapeutically effective amount of selenium, and a therapeutically effective amount of at least one of a triad of amino acids selected from L-alanine, glycine and glutamic acid.

The invention is also directed to a preferred formula comprising the following ingredients each in a therapeutically effective amount: Vitamin C, Vitamin B6, Vitamin E, zinc, glycine, L-alanine, Glutamic acid, Saw palmetto, Pygeum extract, Pumpkin seed, Stinging Nettle, Echinacea, garlic, Ginkgo leaves, and selenium.

The present invention is further directed to administering to a patient a formula comprising at least one antioxidant in a therapeutically effective amount, at least one anti-inflammatory in a therapeutically effective amount, at least one immunity booster in a therapeutically effective amount, phytosterol in a therapeutically effective amount, garlic in a therapeutically effective amount, selenium in a therapeutically effective amount and at least one of a triad of amino acids selected from L-alanine, glycine and glutamic acid.

The present invention is further directed to an all-natural prostate nutritional supplement that alleviates or eliminates the symptoms of prostatitis and lower urinary tract problems, and provides a non-surgical alternative for the treatment of prostatitis and BPH, comprising a formula of at least one antioxidant, at least one anti-inflammatory, at least one immunity booster, pytosterol, garlic, selenium, and at least one of a triad of amino acids selected from L-alanine, glycine and glutamic acid. The preferred formula contains a synergistic blend of fifteen selected herbs, vitamins, minerals, and amino acids, including ginkgo, garlic, Echinacea, glycine, alanine, and glutamic acid.

The efficacy of the formula is thought to be produced by the synergy of the particular components of the invention's formula. The preferred embodiment includes the important herb Echinacea, which is particularly important to the diseased prostate, in concert with garlic, an important anti-inflammatory agent, together with the Chinese triad of amino acids glycine, alanine, and glutamic acid. Also unique to another preferred formula is ginkgo, an herb that improves vascularity and is believed to improve the delivery of the important nutrients to the prostate. The formula has unique prostate penetration and anti-inflammatory response unknown in other medical products.

Beneficial effects can include the elimination or improvement of lower urinary tract symptoms by reducing prostate inflammation and urethra compression by swelling of the prostate, the prevention of the need for inappropriate prostate surgery, (i.e., provide a non-surgical option for prostate care), the possible prevention of prostate cancer, the improvement of a patient's stream size and strength, and the elimination or improvement of symptoms of prostatitis documented by a reduction of prostatic specific antigen (PSA) and expressed prostatic secretion (EPS).

The formula's efficacy was determined by monitoring patients with three tests: the EPS, PSA, and AUA symptom survey. These three tests have been used to track prostate disorders. However, their use in tracking the efficacy of a nutritional supplement is previously unknown.

This formula yields synergistic effects in treating the symptoms associated with BPH and prostatitis. The formula has no known side effects or interactions with medication. The formula has been shown to work in a minimum time of 3 days to 6 weeks.

The objects and advantages of the invention will appear more fully from the following detailed description of the preferred embodiment of the invention made in conjunction with the accompanying drawings.

Figure 4:
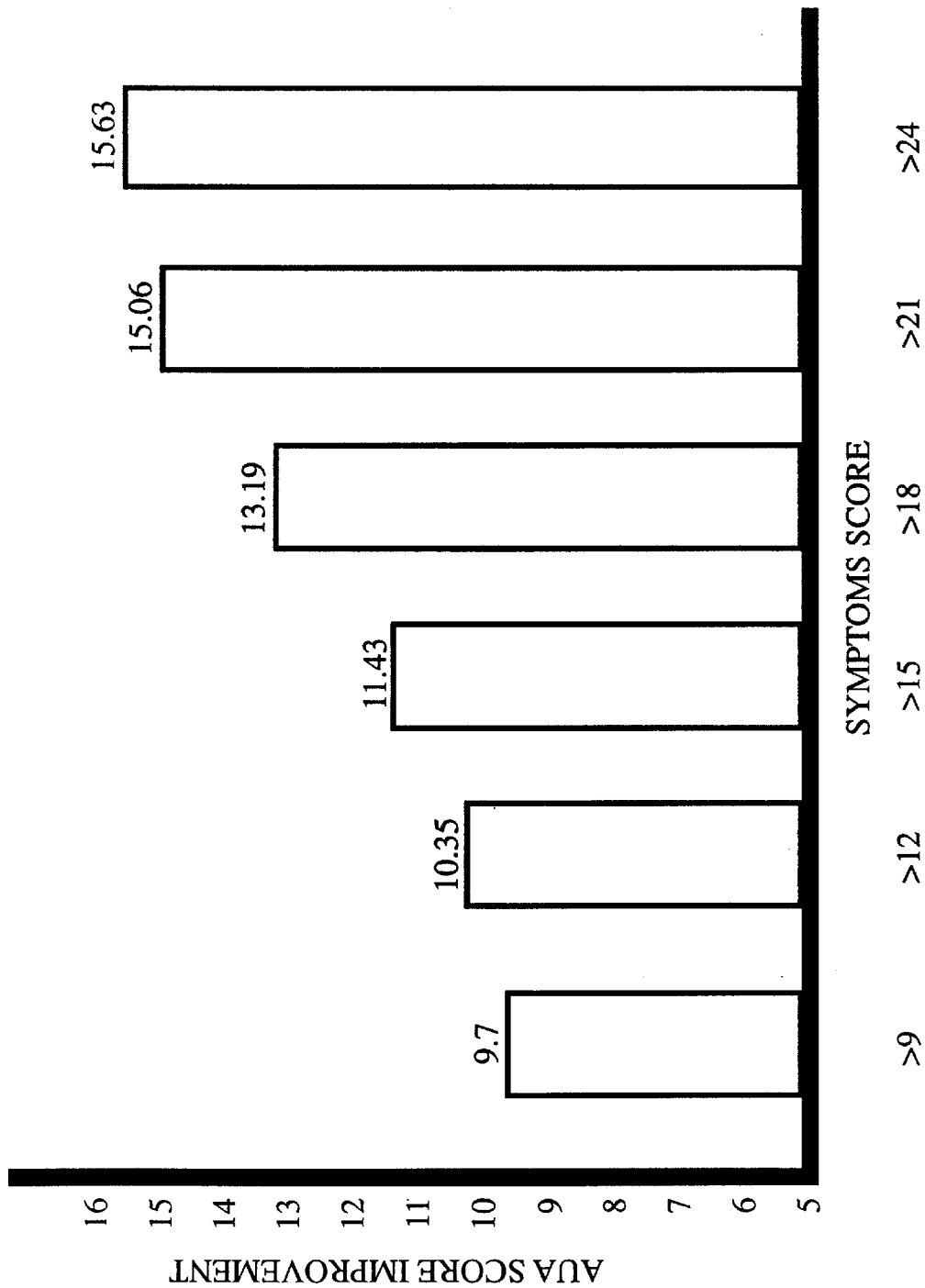
Figure 5:
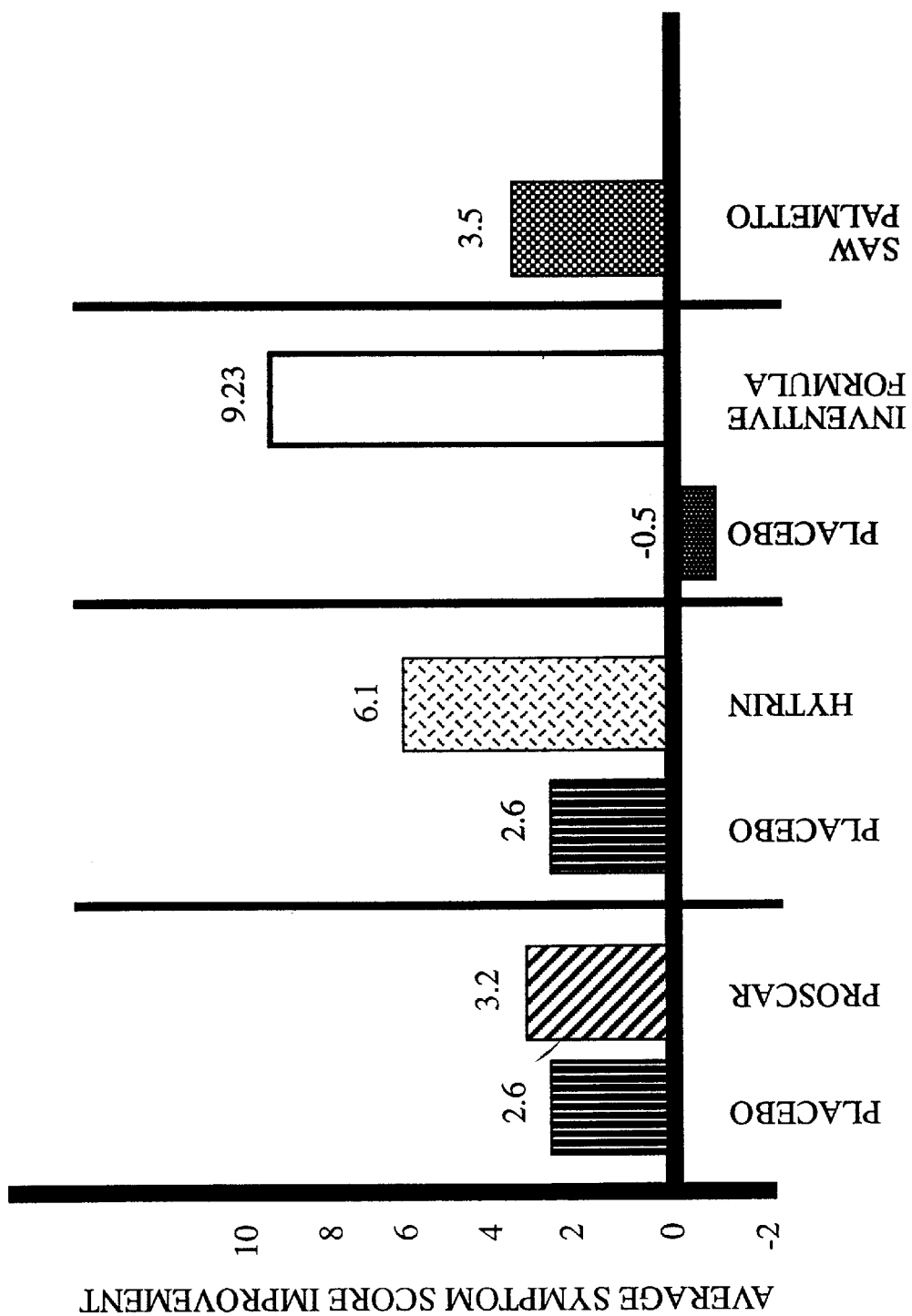

procedures as measured by the average symptom score improvement;

FIG. 4 is a graph depicting symptoms improvement results as measured by a comparison of before use of the inventive formula to after use; and FIG. 5 is a graph comparing American Urology Association (AUA) symptom score results in men using the inventive formula to men using other products or procedures.

DETAILED DESCRIPTION

The prostate formula of the present invention has ingredients selected from several categories including at least one antioxidant, at least one anti-inflammatory agent, at least one immunity booster, phytosterol, garlic, selenium and at least one of a triad of amino acids selected from L-alanine, glycine and glutamic acid.

Antioxidants: Antioxidants neutralize free radicals which can cause cancer. They can have synergistic effects when combined with other ingredients in the formula. Examples of antioxidants include Vitamin E, Vitamin C, Stinging nettle, Echinacea, and pumpkin seed. Antioxidants are present in the formula in amounts ranging from 10 to 40% by weight, preferably in amounts ranging from 15 to 25% by weight, and most preferably about 22% by weight.

Anti-inflammatories: Anti-inflammatories prevent and reduce inflammation. Saw palmetto, garlic, and zinc are examples of anti-inflammatories. Anti-inflammatories are present in the formula in amounts ranging from 2 to 15% by weight, preferably in amounts ranging from 5 to 10% by weight, and most preferably about 7% by weight.

Immunity Boosters: Immunity boosters are vital to allowing the body to heal itself. They can have synergistic effects when combined with other ingredients in the formula. Echinacea, zinc, Vitamin E, Vitamin B6, garlic, Vitamin C, Stinging nettle, Pumpkin seeds, and selenium are examples of immunity boosters. Immunity boosters are present in the formula in amounts ranging from 10 to 40% by weight, preferably in amounts ranging from 15 to 25% by weight, and most preferably about 24% by weight.

Phytosterols: Phytosterols (e.g., sitosterols and stigmasterols) are plant sterols. Sitosterols are the principal sterols of plant oils. They differ from cholesterol chiefly in the presence of an additional ethyl group in the C-17 side chain. Examples of β-sitosterols include cinchol, 5-stigmasten-3β-ol, and (24R)-24-ethyl-5-cholesten-3β-ol. Saw palmetto, pumpkin seed, Stinging nettle, and Pygeum contain phytosterols. Preferably, β-sitosterol is used. Phytosterols are present in the formula in amounts ranging from 10 to 50% by weight, preferably in amounts ranging from 20 to 40% by weight, and most preferably about 27% by weight.

Garlic: Garlic (allicin) is a natural antibiotic that works to improve the host response to infection. It is synergistic with the formula's other ingredients. Garlic contains selenium, is a natural vascular stimulant, lowers cholesterol, lowers the risk of coronary artery disease, and protects against cancer by preventing dietary nitrites from becoming cancer causing nitrosamines. Garlic is present in the formula in an amount ranging from about 0.5 to 10% by weight, preferably 1 to 5% by weight, and most preferably about 2% by weight.

Selenium: Studies show that when the element selenium is administered to men they have 44–66% fewer prostate cancers versus those that do not get selenium. This theoretically occurs because of an improvement in the general health and immunity of the prostate. Selenium is also a natural vascular stimulant and immunity booster. Selenium and Vitamin E are synergistic and boost T cells levels. Selenium is present in the formula in an amount ranging from about 0.5 to 4% by weight, preferably 1 to 3% by weight, and most preferably about 2% by weight.

Amino Acids: The amino acids glutamic acid, L-alanine, and glycine are a Chinese remedy for prostate health and can act synergistically with the other ingredients of the formula. Glutamic acid energizes and counters depression. Glycine also assists in spastic control. Although the listed amino acids have synergistic effects and are preferred to placed in the formula as a group, not all of the amino acids are required. When used in the formula, glycine is present in an amount ranging from about 3 to 15% by weight, preferably 5 to 12% by weight, and most preferably about 10% by weight. When used in the formula, L-alanine is present in an amount ranging from about 0.1 to 5% by weight, preferably 0.5 to 2% by weight, and most preferably about 1% by weight. When used in the formula, glutamic acid is present in an amount ranging from about 3 to 15% by weight, preferably 5 to 12% by weight, and most preferably about 10% by weight.

Ingredients:

Echinacea has been shown to simulate immune response. It also contains several potent antioxidant compounds, such as echinacoside and caffeoyl derivative. When used in the formula, Echinacea is present in an amount ranging from about 0.2 to 5% by weight, preferably 1 to 4% by weight, and most preferably about 2% by weight.

Saw palmetto has been shown to reduce prostatic inflammation and swelling, and improves bothersome urinary symptoms. Saw palmetto inhibits the arachindonic acid cascade. It improves urinary flow, reduces residual bladder urine volume, increases ease in commencing urination, decreases frequency of urination, and decreases the need to empty the bladder at night. It has been shown to alter blood levels of testosterone and decrease the more active form of testosterone (DHT). Saw Palmetto does not alter PSA however. Saw palmetto is the most popular plant product used for prostate problems. Saw palmetto is a source of phytosterol. When used in the formula, Saw palmetto is present in an amount ranging from about 1 to 20% by weight, preferably 5 to 15% by weight, and most preferably about 9% by weight.

Stinging nettle, an antioxidant and a source of Vitamin E and phytosterol, enhances bladder elimination. When used in the formula, Stinging nettle is present in an amount ranging from about 1 to 20% by weight, preferably 4 to 15% by weight, and most preferably about 7% by weight.

Pumpkin seed, an antioxidant, contains essential fatty acids and is a source of zinc and phytosterols. Pumpkin seed is also an anti-inflammatory and is used in the treatment of impotency and swollen prostate. When used in the formula, pumpkin seed is present in an amount ranging from about 5 to 30% by weight, preferably 10 to 25% by weight, and most preferably about 18% by weight.

*Pygeum africanum* (Pygeum) is made from the bark of African evergreen tree. It has been shown to work as an anti-inflammatory agent and improves urinary symptoms. *Pygeum africanus* is used in the treatment of benign prostatic hyperplasia. It is a source of phytosterol. When used in the formula, it is present in an amount ranging from about 4 to 15% by weight, preferably 7 to 12% by weight, and most preferably about 9% by weight.

Gingko biloba has been shown to improve cerebral circulation as well as generalized circulation. When used in the formula, is present in an amount ranging from about 0.5 to 5% by weight, preferably 1 to 3% by weight, and most preferably about 2% by weight.

Vitamin E is known to reduce prostate cancer. Vitamin E is an intermediate metabolite in energy producing pathway at cellular level. It is an immune stimulant that lowers cholesterol, raises good cholesterol (i.e., HDL), protects the nervous system, improves sexual prowess, protects against cardiovascular disease, decreases symptoms of PMS, stabilizes of improves fibrocystic breast disease, and is an anti-oxidant. When used in the formula, Vitamin E is present in an amount ranging from about 1 to 10% by weight, preferably 3 to 8% by weight, and most preferably about 5% by weight. Vitamin E has been shown to in synergy with selenium.

Vitamin B6 is known to boost immunity and is a cancer preventative. When used in the formula, Vitamin B6 is present in an amount ranging from about 1 to 7% by weight, preferably 1 to 6% by weight, and most preferably about 3% by weight.

Vitamin C is known as a cancer preventative, is useful for treatment of some mental disorders, is an anti-oxidant, and is an immunity booster. When used in the formula, Vitamin C is present in an amount ranging from about 0.5 to 5% by weight, preferably 1 to 4% by weight, and most preferably about 2% by weight.

Zinc is known to prevent of prostate cancer and improve the prostatic immune system. It also exerts an anti-inflammatory effect on the prostate. Additionally, zinc has been shown to improve male potency and sex drive, prevent cancer, benefit diabetics and prevent hair loss. When used in the formula, zinc is present in an amount ranging from about 5 to 20% by weight, preferably 7 to 15% by weight, and most preferably about 12% by weight.

Binders and fillers, known to the art, are added to complete the formula. Non-limiting examples of binders and fillers include TABULOS, CAB-O-SIL M5 (Cabot Corporation, Tuscola, Ill.) and magnesium stearate (vegetable grade).

Combining the formula's ingredients synergistically improves the overall benefit and effect of the individual ingredients. For example, zinc benefits from substantial amounts of Vitamin E, selenium, and Vitamin B6, as well as other nutrients to effectively enter and treat the prostate.

The phrase "a therapeutically effective amount" means the amount of the composition that provides a therapeutic benefit in the prevention or improvement of disorders of the prostate, or for maintaining prostate health.

Although any suitable route of administration may be employed for providing the patient with an effective dosage of the composition according to the methods of the present invention, oral administration is preferred. Suitable routes include, for example, oral, rectal, parenteral, intravenous, topical, transdermal, subcutaneous, intramuscular, and similar forms of administration may also be employed. Suitable dosage forms include tablets, troches, dispersions, suspensions, solutions, capsules, patches, suppositories, and the like, although oral dosage forms are preferred. The formula is preferably provided in the form of capsules, preferably 120 capsules per bottle, with a shelf life of 3 years. Indications for use are preferably to "take as directed," or one capsule taken twice per day. A first preferred embodiment of the composition is set forth in the table below:

FORMULA EXAMPLE

| INGREDIENT | ACTIVE | ACTUAL | % BY WT. | CHEMICAL OR SCIENTIFIC NAME | OTHER INFORMATION |
| --- | --- | --- | --- | --- | --- |
| Vitamin C | 20 mg | 20.00 mg | 2 | ascorbic acid | |
| Vitamin B6 | 20 mg | 24.39 mg | 3 | pyridoxine HCl | |
| Vitamin E | 50 IU | 42.19 mg | 5 | d-alpha tocopherol succinate | preferably from soy oil |
| Zinc | 20 mg | 100.00 mg | 12 | Zinc chelate 20% | zinc amino acid chelate |
| Glycine | 91 mg | 91.00 mg | 10 | | preferably from microbiological fermentation |
| L-alanine | 9 mg | 9.00 mg | 1 | L-alanine FCC | |
| Glutamic acid | 91 mg | 91.00 mg | 10 | | preferably from microbiological fermentation |
| Saw Palmetto | 81 mg | 81.00 mg | 9 | Saw Palmetto P/E 25% | preferably containing 13% phytosterols |
| Pygeum extract | 76 mg | 76.00 mg | 9 | *Pygeum africanum* | preferably containing 13% phytosterols |

-continued

FORMULA EXAMPLE

| INGREDIENT | ACTIVE | ACTUAL | % BY WT. | CHEMICAL OR SCIENTIFIC NAME | OTHER INFORMATION |
|---|---|---|---|---|---|
| Pumpkin seed | 152 mg | 152.00 mg | 18 | *Cucurbita pepo* | |
| Stinging nettle leaves | 57 mg | 57.00 mg | 7 | *Urita dioica* | |
| Echinacea | 19 mg | 19.00 mg | 2 | *Echinacea purpurea* | |
| Garlic | 16 mg | 16.00 mg | 2 | Garlic A-1500 *Allium sativa* | (preferably odor controlled) |
| Ginkgo leaves | 17 mg | 17.00 mg | 2 | *Ginkgo biloba* | |
| Selenium | 0.1 mg | 20.0 mg | 2 | Selenium chelate Hvp 0.5% | |
| Tabulos[1] | 40 mg | 40.00 mg | 5 | | |
| Magnesium Stearate (Veg. Grade)[1] | 7.5 mg | 7.50 mg | 1 | | |
| Cabosil CM5[1] | 3.8 mg | 3.80 mg | 0 | | |
| | Totals: | 866.88 | 100 | | |

[1]Ingredients that are fillers or binders

A second preferred embodiment of the composition is one including an active amount of 8 mg of Uva ursi (Artcostaphylus Uva ursi).

Tests Used to Study Inventive Formula

Treatment with the inventive formula improved scores on the three tests, which have been used to detect prostate disorders, including cancer, prostatitis, and BPH: expressed prostatic secretion (EPS), prostatic specific antigen (PSA), and American Urology Association (AUA); and Symptom Index. For the first time, these tests were used to evaluate the effectiveness of a composition on prostate health.

EPS Test. The EPS test, which was originally designed as a test for prostatitis screening, is a microscopic examination of the prostatic fluid or expressed prostatic secretion (EPS). The prostatic secretion is obtained by gentle massage of the prostate during the digital rectal examination. When the fluid is examined under the microscope, a finding of more than 10 white blood cells per high powered field (WBCS/HPF) is considered definitive proof of inflammation and prostatitis.

PSA Test. The PSA test is a blood test. The PSA test can be used to suggest the presence of or monitor prostate cancer. The PSA test can be abnormal with benign prostate disease and infection of the prostate gland, and can be elevated with other conditions that irritate the prostate gland. The prostate specific antigen (PSA) is a protein substance produced by certain cells in the prostate gland. A very small amount of PSA escapes into the blood stream. Thus, PSA can be tested in the blood. Because the amount of PSA in the blood is very low, detection of it requires a very sensitive monoclonal antibody technique. The PSA protein can exist in the blood by itself, or it can join with other substances in the blood. When it is by itself, it is known as free PSA. When it is joined with other substances, it is known as bound or complexed PSA. Total PSA is the sum of free and bound forms, which is what is measured as the standard PSA test.

As described above, PSA was originally designed as a blood test for prostate cancer screening. PSA blood levels of 0–4 were designated as "normal", but this range was arbitrarily selected as a guide for possible prostate cancer screening and does not necessarily indicate a healthy prostate. It is now known that up to 30% of all prostate cancers occur in patients with PSA levels less than 4. Because prostate cancer obviously cannot be considered normal, this suggests that the original "normal" PSA range of 0–4 is much too high. It has been suggested that any PSA level greater than 1 indicates an unhealthy prostate with active prostatitis.

It is well known that prostatitis increases the PSA level. In fact, it is much more likely that any unexplained increase in PSA level is due to prostatitis than to prostate cancer. Many urologists will currently treat their high PSA patients with one month of antibiotics and repeat the PSA level before recommending a biopsy. Only if the second PSA level remains elevated will a biopsy be ordered.

It is believed that a significant percentage of any elevation of PSA level in the blood should be considered prostatitis until proven otherwise. While prostate cancer is certainly a concern and should be considered carefully and appropriately, prostatitis is much more likely. PSA can serve as a very useful marker or indicator of the degree of prostatic inflammation present and help determine the effectiveness of prostatitis therapy.

AUA Symptom Score. The AUA Symptom Score, which was drafted by the American Urologists Association and was validated in 1996, evaluates man's voiding abilities. Symptom Score includes nocturia, frequency, intermittency, incomplete elimination, stream size, urgency, and the need to strain. Respondents answer seven questions about the severity of symptoms, such as the following:

(1) Over the past month, how often have you had the sensation of not emptying your bladder completely after you finished urinating?

(2) Over the past month, how often have you had to urinate again less than 2 hours after you finished urinating?

(3) Over the past month, how often have you found that you stopped and started again several times when you urinate?

(4) Over the past month, how often have you found it difficult to postpone urination?

(5) Over the past month, how often have you had a weak urinary stream?

(6) Over the past month, how often have you had to push or strain to begin urination?

(7) Over the past month, how many times did you most typically get up to urinate from the time you went to bed at night until you got up in the morning?

Respondents indicate the frequency of the events, with each frequency having an assigned score. It is possible to define whether the symptoms are mild (0–7 points), moderate (8–19 points) or severe (20–35 points).

Studies

Figure 1:
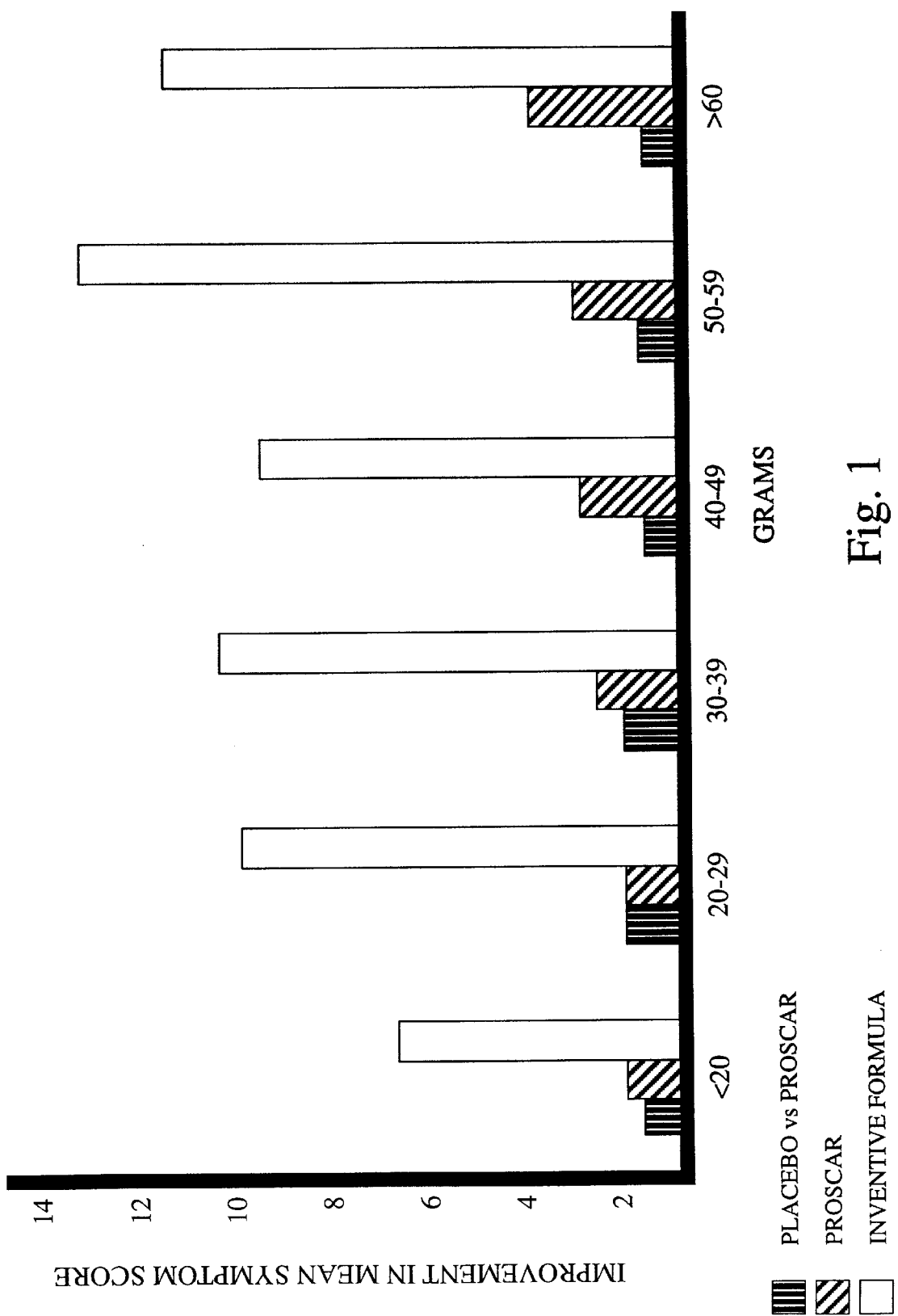
FIG. 1 is a graph comparing results in men using the inventive formula to men using PROSCAR or a placebo as measured by grams of prostate versus the improvement in the mean symptom score achieved.

1. Symptom Response by Prostate Size Study. Another study compared patients give a placebo, PROSCAR, or the inventive formula. The study, compared symptoms response to prostate size. It showed that the larger the prostate, the more effective the formula. The study showed that patients given the inventive formula had greater improvement in mean symptom score than patients given the placebo or PROSCAR. It also showed that the greater the symptoms, the greater the effect that the formula had. These results are summarized in FIG. 1.

2. Study comparing formula to other products or procedures. In a study where the inventive formula was compared to other products or procedures was used in patients with prostate disorders, the patients treated with the inventive formula achieved the best effects when compare to patients receiving other products or procedures. Table 1 summarizes these results.

TABLE 1

Chronic Prostatitis Options

| PRODUCT OR PROCEDURE | EFFECTS ON LUTS[1] VOIDING SYMPTOMS | EFFECTS ON PSA | EFFECTS ON EPS | ABILITY TO CURE | IMPROVED SEXUAL PERFORMANCE |
|---|---|---|---|---|---|
| Antibiotics | 1/2 | 1 | −1/0 | −1/0 | 0 |
| PROSCAR | 1 | −1 | 0 | 0 | −1/0 |
| Alpha-Blockade (HYTRIN, CARDURA & FLOMAX) | 1/2 | 0 | 0 | 0 | −1/0 |
| Surgery (on prostate, any procedure) | 1 | −1/0/1 | 0 | 0 | −1/0 |
| Inventive Formula | 1/2 | 1 | 1/2 | 1 | 1/2 |

[1]LOWER URINARY TRACT SYMPTOMS
Legend: −1 = Negative Effect, 0 = No effect or unknown effect, 1 = Partial effect, 2 = Complete effect.
Comparison assumes antibiotics for a defined period of time and continuous use for PROSCAR, Alpha-Blockade, and the inventive formula.

3. PSA Studies

In a study of fifty-seven prostatitis patients treated with the inventive formula, patients were tested for PSA both before and after treatment. It is well accepted that a PSA of greater than 10 indicated the presence of prostate cancer. The study also used the PSA value of greater than 4 to indicate prostate ill health. All unmarked times were not dated, but all are less than 12 months. Table 2 below shows the PSA reduction that was achieved using the inventive formula.

TABLE 2

PSA Reduction Using Inventive Formula

| Pt.* | PSA Before formula | PSA After History of formula | Pt. | PSA Before formula | PSA After History of formula |
|---|---|---|---|---|---|
| LW | 6.4 | 0.7 | CR | 4.7 | 3.7 |
| TG | 43.0 | 7.4 | BG | 2.5 | 2.1 |
| RD | 16.0 | 3.8 (after 11 months) | GP | 4.1 | 2.8 |
| RV | 2.9 | 2.1 | VJ | 4.5 | 3.6 |
| BC | 2.1 | 0.9 | LV | 15.6 | 5.4 |
| BM | 7.9 | 7.0 | DV | 3.8 | 1.2 |
| HM | 11.4 | 4.6 | JC | 10 | 3.1 |
| CA | 14.0 | 2.7 | CC | 22.0 | 19.0 |
| JS | 8.4 | 4.9 | HF | 5.3 | 4.6 |
| MS | 3.8 | 0.8 | FJ | 7.5 | 5.2 |
| RV | 25.0 | 16.0 (6 months) | RH | 8.5 | 5.4 |
| GS | 6.8 | 4.7 | RA | 2.5 | 2.2 |
| GM | 8.8 | 5.4 | RG | 5.9 | 5.5 |
| DE | 25.3 (biopsy neg.) | 3.0 (8 months) | GH | 36.0 | 1.6 |
| RW | 0.5 | 0.3 (12 months) | JB | 4.6 | 3.9 (9 months) |
| VS | 3.8 | 2.9 | BD | 9.3 | 4.8 (5 months) |
| CC | 5.6 | 4.3 | MS | 7.5 | 5.4 (9 months) |
| BD | 9.3 | 5.9 | RN | 7.0 | 2.1 (8 months) |
| DP | 18.0 | 11.0 (Antibiotics × 6 Wks) | EG | 4.7 | 4.1 (3 months) |
| RL | 7.4 | 4.1 | LL | 2.6 | 1.3 (13 months) |
| CD | 3.6 | 2.4 | DL | 18.0 (biopsy neg × 2) | 10.5 (4 months) |
| JL | 4.0 | 3.5 (4 months) | HK | 5.6 | 2.6 (6 months) |
| LG | 1.3 | 0.9 (12 months) | PH | 1.0 | 0.9 (6 months) |

TABLE 2-continued

PSA Reduction Using Inventive Formula

| Pt.* | PSA Before formula | PSA After History of formula | Pt. | PSA Before formula | PSA After History of formula |
|---|---|---|---|---|---|
| RS | 11.0 | 5.8 (4 months) | AA | 4.5 | 0.8 (9 months) |
| EL | 6.7 | 4.2 (3.5 months) | CC | 5.9 | 3.7 (14 months) |
| ML | 11.4 | 7.4 (3 months) | JA | 7.45 | 4.9 (2 months) |
| CT | 2.6 | 2.0 (5 months) | RA | 0.8 | 0.5 (10 months) |
| LS | 4.1 | 3.4 (10 months) | MH | 20.1 (Biopsy Neg. × 2) | 10.0 (2.5 months) |
| ES | 4.3 | 3.2 (6 months) | | | |

*Patient (Initials in each row signify patient's initials)

Figure 2:
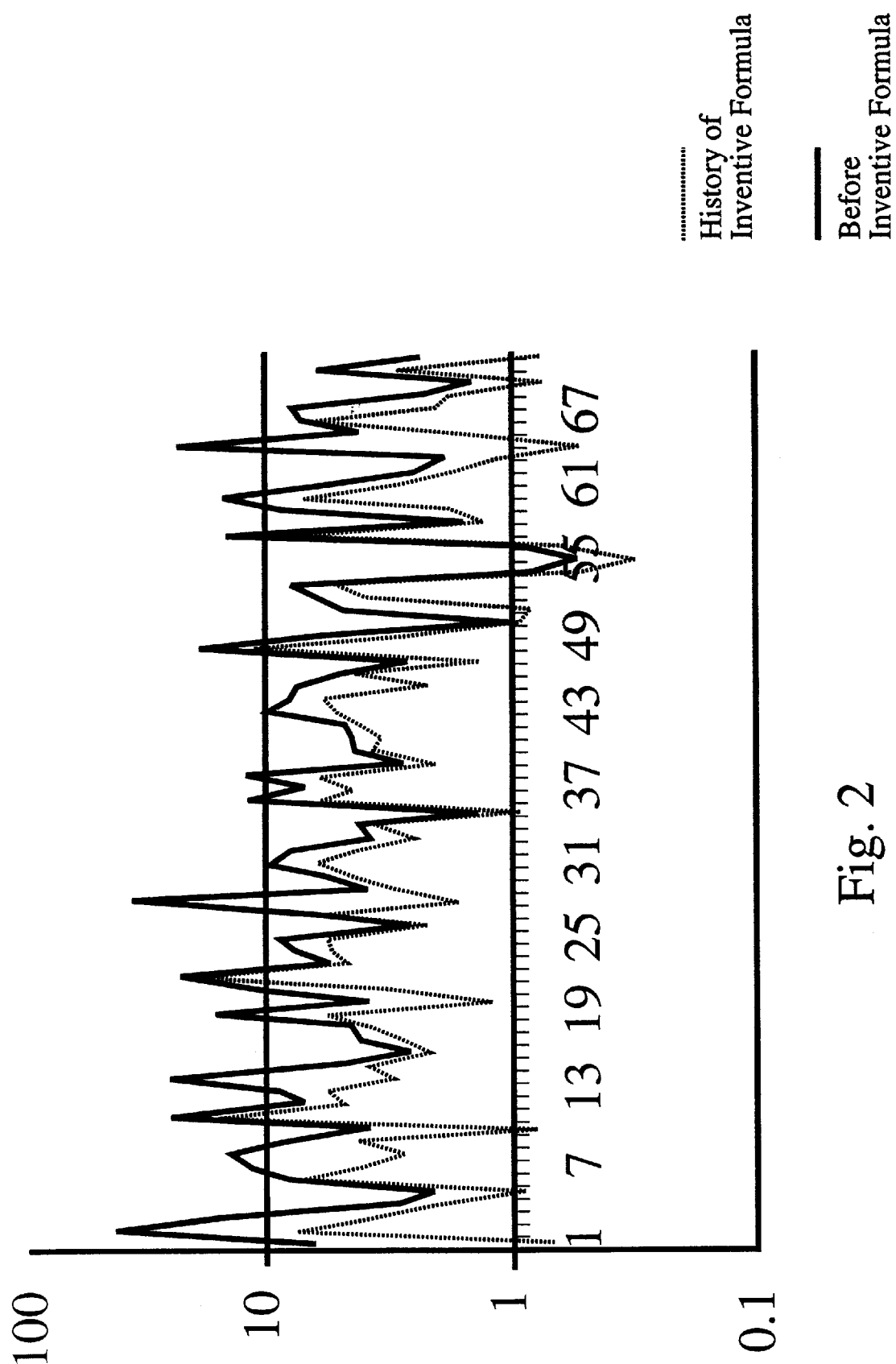
FIG. 2 is a graph depicting prostatic specific antigen (PSA) test results as measured by a comparison of before use of the inventive formula to after use.

FIG. 2 summarizes the PSA results from 70 men, comparing their PSA test results before and after use of the inventive formula. The PSA test results are quantified in ng/ml measurements on the y-axis. All 70 men showed a reduced PSA result after use of the inventive formula. The data displayed in FIG. 2 contains some of the patient results that are shown in Table 2, with FIG. 2 being more complete than Table 2.

4. EPS Studies. Using EPS as a measure of prostate condition, a study was run on 20 patients all having documented prostatitis. Nineteen patients were treated with the inventive formula. One was not. One patient treated with the formula was not analyzed after treatment began. The one patient who did not receive the formula, but received antibiotic treatment instead, had an increase in EPS. As Table 3 shows, in 18 of the 19 treated patients, their EPS was reduced with the inventive formula.

TABLE 3

EPS Reduction Using Inventive Formula

| Pt. | WBCs BEFORE FORMULA | WBCs AFTER FORMULA | LENGTH OF TIME |
|---|---|---|---|
| SP | 100–120 | 25–35 | 1 Month |
| JM | 100–150 | 60–80 | 3 Months |
| JW | 80–100 | 30–50 | 2 Months |
| FR | 200–275 | 150–200 | 1 Month |
| RS | 20–100 | 16–25 | 2.5 Months |
| RA | 25–35 | 8–12 | 2 Months |
| JM | 40–50 | 0–7 | 9.5 Months |
| RG | 100–120 | 75–110 | 2 Months |
| DI | 20–30 | 10–15 | 1.5 Months |
| RD | 18–25 | 4–6 | 1.5 Months |
| MP | TNTC[1] | 50 | 8 Months |
| DP | 60–80 (No Formula) | 80–120 (No Formula) | Antibiotics for 6 Wk |
| RM | 150–200 | 25–35 | 6 Weeks |
| RK | TNTC | 120–140 | 6 Months |
| FB | 35–60 | 8–18 | 4 Months |
| NE | 120–160 | 45–65 | 2 Months |
| JS | 40–50 | 5–9 | 6 Months |
| RH | 100–300 | | |
| JF | 100–120 | 20–30 | 1 Year |
| PH | 80–100 | 40–60 | 6 Months |

[1]TNTC = too numerous to count

Figure 3:
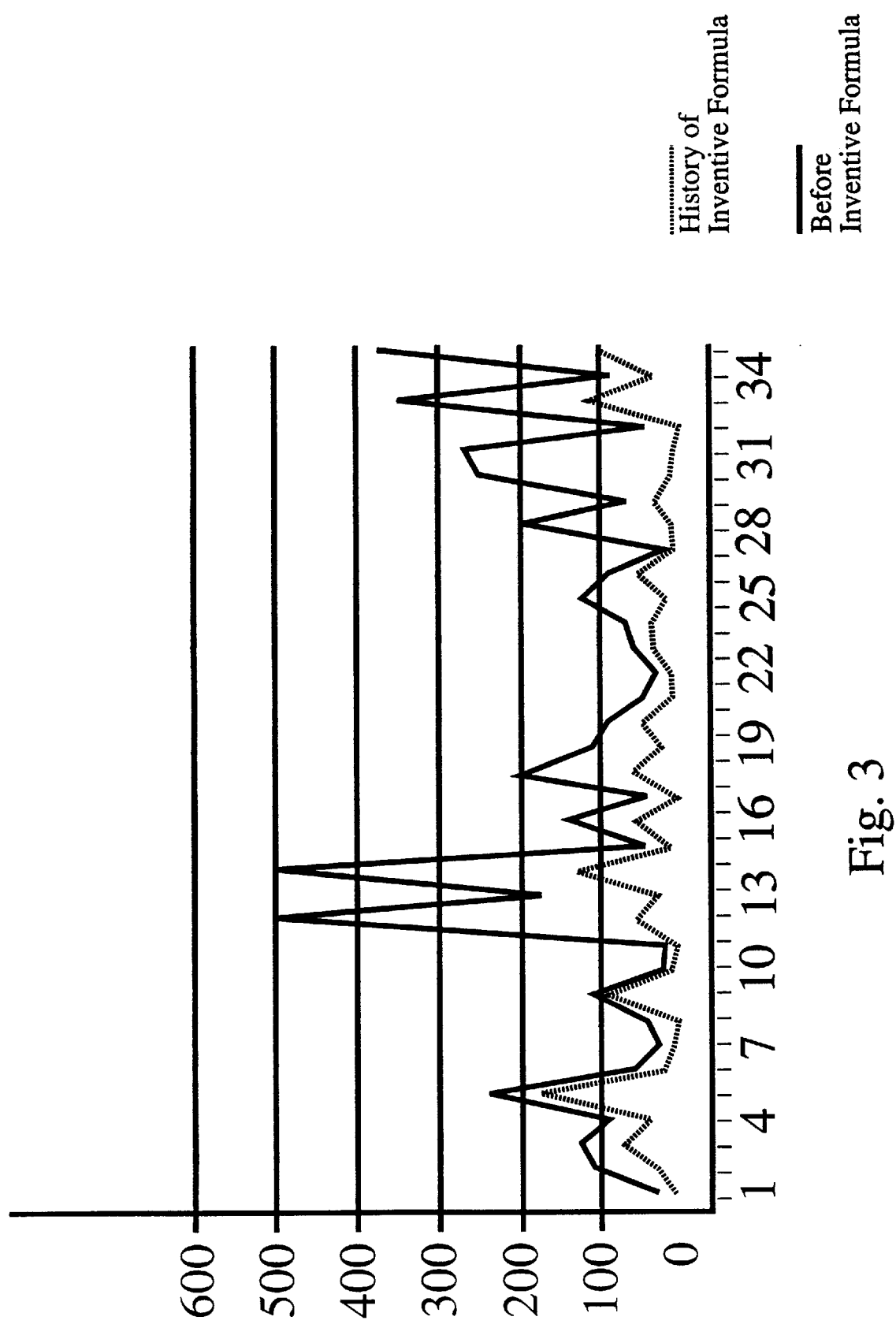
FIG. 3 is a graph depicting expressed prostatic secretion (EPS) test results as measured by a comparison of before use of the inventive formula to after use.

FIG. 3 graphically displays the EPS test results from 35 men, comparing their EPS test result before and after use of the inventive formula, on improvement in prostate inflammation on the inventive formula. The EPS test results are quantified in WBCS/HPF on the y-axis. For convenience, the two men who had a WBCS/HPF of too numerous to count (TNTC) are graphed at 500 WBCS/HPF. All 35 men had reduced WBCS/HPF after use of the inventive formula. The data displayed in FIG. 3 contains some of the patient results that are shown in Table 3, with FIG. 3 being more complete than Table 3.

5. AUA Symptom Score Study. Using AUA Symptom Score as a measure of prostate condition, 102 men's AUA symptom scores were evaluated before and after use of the inventive formula. Test results are summarized in Table 4 below.

TABLE 4

| Pt. | AUA Symptom Score Before Invention | AUA Symptom Score After Invention | Improvement Number (%) | Time To Improvement/ Review | History Of Other Meds. |
|---|---|---|---|---|---|
| D. M. | 18/19 (18.5) | 4 | 14.5 (79%) | 2 weeks | |
| S. C. | 6 | 3 | 3 (50%) | 4 weeks | |
| D. Y. | 7/8 (7.5) | 2 | 5.5 (74%) | 3 weeks | |
| C. F. | 23/24 (23.5) | 16.5 | 7 (30%) | 3 weeks | |
| T. K. | 17 | 10.5 | 6.5 (39%) | 4 weeks | |
| C. C. | 15/16 (15.5) | 7 | 8.5 (55%) | 8 weeks | |
| W. P. | 17 | 7 | 10 (59%) | 7 weeks | HYTRIN |
| P. R. | 17 | 9 | 8 (47%) | 6 weeks | |
| W. P. H | 25 | 16 | 9 (36%) | 7 weeks | |
| C. B. | 23 | 10.5 | 12.5 (55%) | 2 weeks | |
| O. B. M. | 9 | 2 | 7 (78%) | 6 weeks | |
| J. B. | 22/23 (22.5) | 10 | 12.5 (56%) | 4 weeks | |
| R. W. | 16/17 (16.5) | 8.5 | 8 (49%) | 5 weeks | |
| D. E. | 14 | 2 | 12 (86%) | 1 week | |
| W. B. | 13/14 (13.5) | 4 | 9.5 (71%) | 3 weeks | |
| B. B. | 25/26 (25.5) | 15.5 | 10 (40%) | 4 weeks | |
| T. C. | 8/9 (8.5) | 3.5 | 5 (59%) | 4 weeks | |
| W. D. | 20 | 4.5 | 15.5 (78%) | 10 weeks | |

TABLE 4-continued

| Pt. | AUA Symptom Score Before Invention | AUA Symptom Score After Invention | Improvement Number (%) | Time To Improvement/ Review | History Of Other Meds. |
|---|---|---|---|---|---|
| P. B. | 11.5 | 3.5 | 8 (70%) | 5 weeks | |
| C. G. | 21.5 | 12.5 | 9 (42%) | 5 weeks | |
| G. A. | 14 | 4.5 | 9.5 (68%) | 4 weeks | |
| C. T. | 15.5 | 2.5 | 13.0 (84%) | 6 weeks | |
| M. C. | 22 | 15.5 | 6.5 (30%) | 2 weeks | |
| T. G. | 15 | 2 | 13 (87%) | 5 weeks | |
| C. B. | 17.5 | 5 | 12.5 (72%) | 4 weeks | |
| N. D. | 10 | 3 | 7 (70%) | 5 weeks | |
| M. S. | 14 | 3 | 11 (79%) | 8 weeks | |
| B. G. | 10 | 5 | 5 (50%) | 7 weeks | |
| J. B. | 17 | 5.5 | 11.5 (68%) | 5 weeks | HYTRIN |
| G. H. | 21.5 | 2 | 19.5 (91%) | 3 weeks | |
| B. H. | 21 | 4.5 | 16.5 (79%) | 8 weeks | CARDURA |
| J. C. | 13 | 7.5 | 5.5 (43%) | 8 weeks | |
| H. F. | 9 | 1 | 8 (89%) | 7 weeks | |
| D. W. | 17.5 | 7 | 10.5 (60%) | 8 weeks | |
| G. L. | 17 | 3 | 14 (83%) | 3 weeks | |
| B. C. | 17 | 6.5 | 10.5 (62%) | 7 weeks | |
| H. L. | 16 | 6 | 10 (63%) | 5 weeks | |
| M. J. | 18.5 | 7.5 | 11 (60%) | 6 weeks | |
| C. F. | 23.5 | 12 | 11.5 (49%) | 8 weeks | |
| C. F. | 12 | 6 | 6 (50%) | 4 weeks | |
| R. H. | 28.5 | 12.5 | 16 (57%) | 5 weeks | |
| G. G. | 20.5 | 7 | 13.5 (66%) | 5 weeks | |
| R. C. | 11.5 | 3.5 | 8 (70%) | 3 weeks | |
| K. N. | 13.5 | 2.5 | 11 (82%) | 6 weeks | |
| H. D. | 8.0 | 0 | 8 (100%) | 7 weeks | |
| J. C. | 12 | 2.5 | 9.5 (80%) | 7 weeks | |
| E. J. | 11 | 5 | 6 (55%) | 4 weeks | |
| R. J. | 16 | 3.5 | 12.5 (79%) | 10 weeks | |
| R. J. | 11 | 3 | 8 (73%) | 7 weeks | Insulin |
| S. B. | 18.5 | 12.5 | 6 (33%) | 6 weeks | CARDURA |
| R. F. | 15 | 3 | 12 (80%) | 10 weeks | |
| B. M. | 15.5 | 5.5 | 10 (65%) | 6 weeks | |
| T. C. | 13.5 | 4 | 9.5 (71%) | 8 weeks | |
| C. C. | 15.5 | 7 | 8.5 (55%) | 8 weeks | |
| C. C. | 7 | 0.5 | 6.5 (93%) | 8 weeks | |
| D. J. | 23.5 | 10 | 13.5 (57%) | 16 weeks | |
| J. H. | 15 | 1 | 14 (94%) | 8 weeks | |
| M. B. | 14.5 | 4.5 | 10 (69%) | 9 weeks | |
| A. P. | 16 | 2.5 | 13.5 (85%) | 16 weeks | |
| C. R. | 20 | 7 | 13 (65%) | 6 weeks | |
| C. C. | 9 | 5 | 4 (45%) | | HYTRIN 10 mg |
| C. C. | 17 | 4.5 | 12.5 (74%) | 7 weeks | |
| B. C. | 24.5 | 16 | 8.5 (35%) | 7 weeks | |
| B. S. | 9.5 | 2.5 | 7 (74%) | 6 weeks | |
| T. K. | 17 | 3.5 | 12.5 (74%) | 18 weeks | |
| L. S. | 12 | 7.5 | 4.5 (38%) | 4 weeks | |
| K. B. | 16.5 | 5.5 | 11 (67%) | 7 weeks | HYTRIN/Other Herbs |
| P. M. | 13.5 | 3.5 | 10 (74%) | 8 weeks | PROSCAR |
| L. C. | 25 | 4.5 | 21.5 (86%) | 5 weeks | |
| B. S. | 16.5 | 7.5 | 9.0 (55%) | 6 weeks | |
| L. L. | 14.5 | 0.5 | 14 (97%) | 6 weeks | |
| B. W. | 11 | 2.5 | 8.5 (78%) | 7 weeks | |
| D. B. | 8.5 | 0.5 | 8 (95%) | 12 weeks | |
| R. D. | 11.5 | 3.5 | 8 (70%) | 7 weeks | Diabetes |
| R. F. | 19 | 6 | 13 (68%) | 7 weeks | |
| S. M. | 10.5 | 2.5 | 8 (76%) | 6 weeks | Hx. Saw Palmetto 320 mgm QD |
| S. B. | 18.5 | 11.5 | 7 (38%) | 18 weeks | CARDURA 2 mgm (HTN) |
| B. W. | 17.5 | 5.5 | 12 (69%) | 6 weeks | |
| D. G. | 16.5 | 8.5 | 8 (48%) | 19 weeks | Prostatitis |
| S. B. | 16.5 | 6.5 | 10 (61%) | 8 weeks | Prostatitis |
| G. H. | 15.5 | 6 | 9.5 (61%) | 19 weeks | Hx. HYTRIN & Hx. PROSCAR |
| C. B. | 9 | 2 | 7 (78%) | 16 weeks | Hx. Of TURP* |
| R. R. | 10.5 | 0 | 10.5 (100%) | 12 weeks | Prostatitis |
| J. B. | 22 | 5 | 17 (77%) | 22 weeks | CARDURA, HYTRIN/CIPRO# PROSCAR/Saw Palmetto |
| J. S. | 17 | 1.5 | 15.5 (91%) | 7 weeks | Hx. TURP |
| J. M. | 11.5 | 4.5 | 7 (61%) | 6 weeks | Prostatitis |

TABLE 4-continued

| Pt. | AUA Symptom Score Before Invention | AUA Symptom Score After Invention | Improvement Number (%) | Time To Improvement/ Review | History Of Other Meds. |
|---|---|---|---|---|---|
| K. E. | 12.5 | 2 | 10.5 (84%) | 22 weeks | |
| R. V. | 14 | 2.5 | 11.5 (82%) | 18 weeks | |
| B. B. | 25.5 | 3.5 | 22 (86%) | 18 weeks | Hx. Saw Palmetto |
| J. B. | 16.5 | 4 | 12.5 (76%) | 18 weeks | Prostatitis |
| D. P. | 13.5 | 4.5 | 9 (67%) | 6 weeks | |
| R. G. | 15.5 | 5.5 | 10 (65%) | 10 weeks | Diabetes, PROSCAR, HYTRIN (HTN) |
| P. M. | 8.5 | 0.5 | 8 (94%) | 22 weeks | |
| C. L. | 13 | 2 | 11 (85%) | 15 weeks | |
| A. H. | 12.5 | 2 | 10.5 (84%) | 5 weeks | FLOMAX**, Diabetes, Prostatitis |
| B. G. | 10.0 | 2.5 | 7.5 (75%) | 20 weeks | Diabetes, HYTRIN 5 mgm |
| J. W. | 10.5 | 1.5 | 9 (86%) | 10 weeks | Prostatitis |
| G. H. | 11 | 1.5 | 9.5 (86%) | | |
| W. B. | 13 | 2 | 11 (85%) | 24 weeks | |
| M. B. | 15 | 1.5 | 13.5 (90%) | 24 weeks | |
| B. C. | 11.5 | 1.5 | 10 (87%) | 9 weeks | |
| D. L. | 18.5 | 5.5 | 13 (70%) | 20 weeks | |
| K. B. | 5.5 | 0 | 5.5 (100%) | 12 weeks | Prostatitis |
| C. C. | 16.5 | 8.5 | 8 (42%) | | Prostate Ca |
| R. M. | 11 | 2.5 | 8.5 (77%) | | Prostatitis |

*TransUrethral Resection of Prostate
**(tamsulosin HCl, Boehringer Ingelheim Pharmaceuticals, Inc., Ridgefield, Connecticut)
(ciprofloxacin, Bayer Corporation, West Haven, Connecticut)

The data in the Table 4 amplifies the data in FIG. 4, which shows that the greater the pretreatment symptom score, the greater the AUA improvement. In an effort to further qualify the effectiveness of the formula, a prospective, randomized, double blind, placebo controlled AUA study was conducted. The formula was shown to be statistically and clinically significant. All men in the study improved 3 of 7 voiding symptom categories. Fifty percent improved in 6 of 7 categories. Sixty-nine percent of the men improved 6 or 7 of 7 categories. In a follow up to the study, more than 300 men were evaluated using the three tests, EPS, PSA, and AUA. The average improvement in voiding symptom score (AUA) was approximately 13 points. The PSA, a barometer of prostate health, improved in all patients by an average of 43%, while the EPS, our most sensitive marker for prostatitis, noted a 65% reduction in white blood cells. There were no side effects or drug interactions noted during testing or clinical follow-up.

6. FIG. 5 depicts a comparison of non-surgical prostate options versus voiding symptoms. Each option (except for Saw Palmetto) was compared to a placebo. As FIG. 5 shows, the inventive formula produced the greatest improvement in average symptom score.

PATIENT EXAMPLES

Example 1

A classic example of a typical patient's experience involves a 65 year old man who had noted a PSA of 18. His urologist appropriately performed an ultrasound examination and prostate biopsy. The result was chronic prostatitis with no evidence of cancer. Antibiotics were given, but no other therapy was offered. His PSA was repeated after 6 months and found to be unchanged, which is not surprising considering that only 5% of cases of prostatitis are actually caused by bacteria which are potentially curable with antibiotics. The patient underwent a second prostate biopsy, which again showed only chronic prostatitis. When the patient asked his doctor what he could do, the urologist offered to repeat the PSA in another 6 months and consider an additional biopsy then. The patient then began using the inventive formula. In only 3 months, his PSA was reduced by almost half.

Example 2

A 50 year old male was placed on the formula. His original AUA symptom score was 18/19, while his EPS showed 18–25 WBCS/HPF. At the six week mark (per study protocol) an AUA symptom score was performed, which was now 4. The EPS was 4–6 WBCS/HPF. The improved patient has been cleared of any residual prostatitis.

Example 3

A 49 year old male was examined in January of 1999. His PSA history was 7.1. His previous prostate ultrasound and biopsy revealed no evidence of cancer but rather chronic prostatitis. The initial AUA system score was 18 to 19, the EPS range was 20 to 75 WBCS/HPF. This patient received only the prostate nutritional product of the present invention. Within 6 weeks the AUA symptom score reduced to 7–8. At 4 months, the PSA had dropped to 1.9 (normal is 0–4 nanograms per ml). The EPS at 6 months had improved to 6 to 15 WBCS/HPF.

Women can also benefit from the formula of the present invention. The blend of antioxidants and immunity boosters benefit an adult of either sex. Moreover, Uva ursi and Stinging Nettle are bladder stabilizing herbs than can benefit either sex.

It is understood that the invention is not confined to the particular construction and arrangement of parts herein illustrated and described, but embraces such modified forms thereof as come within the scope of the following claims.

What is claimed:

1. A composition for prevention or improvement of prostate disorders or for maintaining prostate health, comprising:
   a. Vitamin C in an active amount of about 0.5 to 5% by weight;
   b. Vitamin B6 in an active amount of about 1 to 7% by weight;
   c. Vitamin E in an active amount of about 1 to 10% by weight;
   d. zinc in an active amount of about 5 to 20% by weight;
   e. glycine in an active amount of about 3 to 15% by weight;
   f. L-alanine in an active amount of about 0.1 to 5% by weight;
   g. Glutamic acid in an active amount of about 3 to 15% by weight;
   h. Saw palmetto in an active amount of about 1 to 20% by weight;
   i. Pygeum extract in an active amount of about 4 to 15% by weight;
   j. Pumpkin seed in an active amount of about 5 to 30% by weight;
   k. Stinging nettle in an active amount of about 1 to 20% by weight;
   l. Echinacea in an active amount of about 0.2 to 5% by weight;
   m. garlic in an active amount of about 0.5 to 10% by weight;
   n. Ginkgo leaves in an active amount of about 0.5 to 5% by weight; and
   o. selenium in an active amount of about 0.5 to 4% by weight.

2. The composition of claim 1, further comprising Uva ursi in an active amount of 8 mg.

3. The composition of claim 1, wherein
   a. the Vitamin C in an active amount of about 1 to 4% by weight;
   b. Vitamin B6 in an active amount of 1 to 6% by weight;
   c. Vitamin E in an active amount of 3 to 8% by weight;
   d. zinc in an active amount of 7 to 15% by weight;
   e. glycine in an active amount of 5 to 12% by weight;
   f. L-alanine in an active amount of 0.5 to 2% by weight;
   g. Glutamic acid in an active amount of 5 to 12% by weight;
   h. Saw palmetto in an active amount of 5 to 15% by weight;
   i. Pygeum extract in an active amount of 7 to 12% by weight;
   j. Pumpkin seed in an active amount of 10 to 25% by weight;
   k. Stinging nettle in an active amount of 4 to 15% by weight;
   l. Echinacea in an active amount of 1 to 4% by weight;
   m. garlic in an active amount of 1 to 5% by weight;
   n. Ginkgo leaves in an active amount of, preferably 1 to 3% by weight; and
   o. selenium in an active amount of 1 to 3% by weight.

4. The composition of claim 3, further comprising Uva ursi in an active amount of 8 mg.

5. The composition of claim 3, wherein
   a. the Vitamin C in an active amount of about 2% by weight;
   b. Vitamin B6 in an active amount of about 3% by weight;
   c. Vitamin E in an active amount of about 5% by weight;
   d. zinc in an active amount of about 12% by weight;
   e. glycine in an active amount of about 10% by weight;
   f. L-alanine in an active amount of about 1% by weight;
   g. Glutamic acid in an active amount of about 10% by weight;
   h. Saw palmetto in an active amount of about 9% by weight;
   i. Pygeum extract in an active amount of about 9% by weight;
   j. Pumpkin seed in an active amount of about 18% by weight;
   k. Stinging nettle in an active amount of about 7% by weight;
   l. Echinacea in an active amount of about 2% by weight;
   m. garlic in an active amount of about 2% by weight;
   n. Ginkgo leaves in an active amount of about 2% by weight; and
   o. selenium in an active amount of about 2% by weight.

6. The composition of claim 5, further comprising Uva ursi in an active amount of 8 mg.

7. A method of prevention or improvement of prostate disorders or for maintaining prostate health, comprising administering the composition of claim 3.

8. A method of preventing or improving prostatitis comprising administering the composition of claim 3.

9. A method of prevention or improvement of prostate disorders or for maintaining prostate health, comprising administering the composition of claim 5.

10. A method of prevention or improvement of prostate disorders or for maintaining prostate health, comprising administering the composition of claim 1.

11. A method of preventing or improving prostatitis comprising administering the composition of claim 1.

12. A composition for prevention or improvement of prostate disorders or for maintaining prostate health, comprising:
    a. Vitamin C in an active amount of 20 mg;
    b. Vitamin B6 in an active amount of 20 mg;
    c. Vitamin E in an active amount of 50 international units;
    d. zinc in an active amount of 20 mg;
    e. glycine in an active amount of 91 mg;
    f. L-alanine in an active amount of 9 mg;
    g. Glutamic acid in an active amount of 91 mg;
    h. Saw palmetto in an active amount of 81 mg;
    i. Pygeum extract in an active amount of 76 mg;
    j. Pumpkin seed in an active amount of 152 mg;
    k. Stinging nettle in an active amount of 57 mg;
    l. Echinacea in an active amount of 19 mg;
    m. garlic in an active amount of 16 mg;
    n. Ginkgo leaves in an active amount of 17 mg; and
    o. selenium in an active amount of 0.1 mg.

13. The composition of claim 12, further comprising Uva ursi in an active amount of 8 mg.

14. A method of prevention or improvement of prostate disorders or for maintaining prostate health, comprising administering the composition of claim 12.

15. The method of claim 14, wherein the prostate disorder that is prevented or improved is prostatitis.

16. The method of claim 14, wherein the administration of the composition improves at least one of expressed prostatic secretion test, prostatic specific antigen test, and American Urologists Association symptom survey.

* * * * *